United States Patent [19]

DeCamp et al.

[11] Patent Number: 4,826,999

[45] Date of Patent: May 2, 1989

[54] HYDROGENATION PROCESS FOR THE FORMATION OF 3,5-DIHYDRO HMG-COA REDUCTASE INHIBITORS

[75] Inventors: Ann E. DeCamp, New Providence; Thomas R. Verhoeven, Cranford; Ichiro Shinkai, Westfield, all of N.J.

[73] Assignee: Merck & Co., Inc., Rahway, N.J.

[21] Appl. No.: 92,803

[22] Filed: Sep. 3, 1987

[51] Int. Cl.$^4$ ...................... C07D 309/30; C07F 7/18
[52] U.S. Cl. ...................... 549/214; 549/292
[58] Field of Search ...................... 549/214, 292

[56] References Cited

U.S. PATENT DOCUMENTS 4,351,844  9/1982  Patchett et al. ...................... 549/292

OTHER PUBLICATIONS

Kuo et al., "Reduction Transformation and, etc" JOC 48, 1991 (1983).

Schrach et al., "Catalytic Hydrogenation Using, etc" CA 85:123066p (1976).
Crabtree et al. I, "Cationic Iridium Diolefin, etc" CA 88:31361q (1978).
Crabtree et al. II, "Occurrence and Origin, etc" *Organometallics* 2 682 (1983).
Evans et al., "Rhodium(I)-Catalyzed, etc" *JACS*, 106, 3866 (1984).
Santos et al., "Catalytic Activity and Visible, "etc. CA 100:180758t (1984).

*Primary Examiner*—Richard L. Raymond
*Attorney, Agent, or Firm*—Melvin Winokur; Joseph F. DiPrima

[57] ABSTRACT

A novel hydrogenation process, using a homogenous iridium or rhodium catalyst for selectively adding hydrogen to the 3,5 positions in the polyhydronaphthyl ring of lovastatin, simvastatin or C-8-acyl or C-6-substituted analogs thereof, is disclosed.

18 Claims, No Drawings

HYDROGENATION PROCESS FOR THE FORMATION OF 3,5-DIHYDRO HMG-COA REDUCTASE INHIBITORS

BACKGROUND OF THE INVENTION

Mevinolin, also known as Lovastatin is a potent HMG-CoA reductase inhibitor and as such is an effective antihypercholesterolemic agent. Patchett et al. (U.S. Pat. No. 4,351,844) have found that a 3,5-dihydrolovastatin (I) is also a potent HMG-CoA reductase inhibitor.

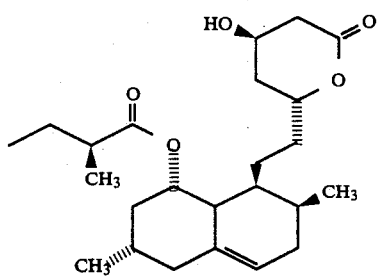

Patchett, et al., supra, describe a catalytic hydrogenation process, employing palladium on calcium carbonate in absolute ethanol, for the reduction of lovastatin to a compound of structure (I). This process has also been described by Kuo et al. J. Org. Chem, 48, 1991(1983). This palladium catalyzed hydrogenation has been described as yielding the 3,5 dihydrolovastatin together with varying amounts of the 3,4-dihydro isomer as a contaminant. Kuo et al, supra, also describe an alternative procedure for the synthesis of compound I vis-vis the treatment of tertbutyldimethylsilyl-lovastatin with triethyl silane in methylene chloride followed by protolysis with trifluoroacetic acid. However, this process requires silylation-desilylation and results in low yields of the desired 3,5-dihydro reduction product.

DETAILED DESCRIPTION OF THE INVENTION

The novel process of this invention may be depicted as:

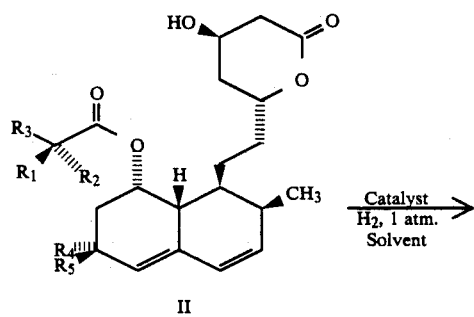

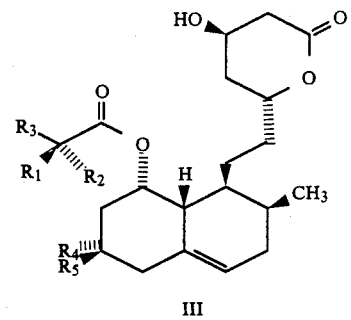

wherein:
$R_1$ is H or $C_{1-3}$alkyl;
$R_2$ is H or $C_{1-3}$alkyl;
$R_3$ is $C_{1-5}$alkyl, phenyl, or $C_{3-7}$ cycloalkyl; or $C_{1-5}$alkyl or phenyl substituted with a group Y where Y is a group not reduced by the catalyst herein, examples of such a group Y are:
(a) t-$C_4H_9$(Me)$_2$SiO—;
(b) halogen (F, Cl or Br);
(c) trifluoromethyl;
(d) $C_{1-3}$ alkoxy;
(e) $C_{1-3}$alkylcarbonyloxy;
(f) phenylcarbonyloxy;
(g) $C_{1-3}$alkoxycarbonyl; or
(h) phenyloxycarbonyl.
$R_4$ is H or $CH_3$ or $CH_2OSi(Me)_2$t-$C_4H_9$ or $OSi(Me)_2$t-$C_4H_9$;
$R_5$ is H or $CH_2OSi(Me)_2$t-$C_4H_9$ or $OSi(Me)_2$t-$C_4H_9$; provided that when either $R_4$ or $R_5$ is $CH_2OSi(Me)_2$t-$C_4H_9$ the other is H; and one and only one of $R_4$ and $R_5$ can be $OSi(Me)_2$t-$C_4H_9$.
Alternatively $R_4$ and $R_5$ may be represented as:
$R_4$ is H or $CH_3$ or $CH_2OSi(Me)_2$t-$C_4H_9$;
$R_5$ is H or $CH_2OSi(Me)_2$t-$C_4H_9$;
provided that at least one of $R_4$ or $R_5$ is H.
Catalyst is [Ir(COD)PCy$_3$(pyr)]PF$_6$ or [Rh(NBD)(DIPHOS-4)]BF$_4$; and
Solvent is dichloromethane, chloroform, chlorobenzene or a like substance;
Tert-butyldimethylsilyl is shown as a hydroxyl protecting group, it will be clear to those skilled in the art that other hydroxyl protecting groups such as tert-butyldiphenylsilyl trimethylsilyl, triethylsilyl, triisopropylsilyl and tetrahydropyranyl could be substituted for tert-butyldimethylsilyl without effecting the outcome of the instant invention.

The instant process selectively adds hydrogen to the 3,5 positions in the polyhydronaphthyl ring of lovastatin, simvastatin or C-8 acyl or C-6 substituted analogs thereof. A homogenous iridium or rhodium catalyst as described herein, is, in the absence of a hydroxyl coordination site at the C-8 position, able to distinguish between a 1,2 and a 1,4 hydrogenation, allowing only the 1,4 reduction under the herein described conditions. The 3,5-dihydro-product is formed in high yield uncontaminated by any other dihydro isomer.

One embodiment of the present invention is the preparation of compounds of structure (III) wherein:
$R_1$ is methyl,
$R_2$ is H or $C_{1-3}$alkyl,
$R_3$ is $C_{1-5}$alkyl, phenyl, or $C_{3-7}$cycloalkyl; or $C_{1-5}$alkyl or phenyl substituted with a group Y where Y is a group not reduced by the catalyst such as (a) t-$C_4H_9(Me)_2SiO-$;
(b) halogen (F, Cl or Br);
(c) trifluoromethyl;
(d) $C_{1-3}$alkoxy;
(e) $C_{1-3}$alkylcarbonyloxy;
(f) phenylcarbonyloxy;
(g) $C_{1-3}$alkoxycarbonyl;
(h) phenyloxycarbonyl.

$R_4$ is $CH_3$; and
$R_5$ is H.

In one class of this embodiment, $R_3$ is $C_{1-5}$alkyl
In a subclass are compounds (III) wherein:
a. $R_2$ is H and $R_3$ is $CH_3CH_2$.
b. $R_2$ is $CH_3$ and $R_3$ is $CH_3CH_2$.

A second embodiment is the preparation of compounds of structure (III) wherein:
$R_1$ is methyl,
$R_2$ is H or $C_{1-3}$alkyl,
$R_3$ is $C_{1-5}$alkyl, phenyl, or $C_{3-7}$cycloalkyl; or $C_{1-5}$alkyl or phenyl substituted with a group Y where Y is a group not reduced by the catalyst such as
(a) t-$C_4H_9(Me)_2SiO-$;
(b) halogen (F, Cl or Br);
(c) trifluoromethyl;
(d) $C_{1-3}$ alkoxy;
(e) $C_{1-3}$alkylcarbonyloxy
(f) phenylcarbonyloxy;
(g) $C_{1-3}$alkoxycarbonyl;
(h) phenyloxycarbonyl.

$R_4$ is H or $CH_2OSi(Me)_2t-C_4H_9$;
$R_5$ is H or $CH_2OSi(Me)_2t-C_4H_9$; provided that at least one of $R_4$ and $R_5$ is H.

In one class of this embodiment, $R_2$ is H or $CH_3$, and $R_3$ is $CH_3CH_2$.

In a subclass are compounds (III) wherein:
a. $R_2$ is H, $R_4$ is $CH_2OSi(Me)_2$—$C_4H_9$, $R_5$ is H.
b. $R_2$ is H, $R_4$ is H, $R_5$ is $CH_2OSi(Me)_2t-C_4H_9$.
c. $R_2$ is $CH_3$, $R_4$ is $CH_2OSi(Me)_2t-C_4H_9$, $R_5$ is H.
d. $R_2$ is $CH_3$, $R_4$ is H; $R_5$ is $CH_2OSi(Me)_2t-C_4H_9$.

A third embodiment is the preparation of compounds of structure (III) wherein:
$R_1$ is methyl,
$R_2$ is H or $C_{1-3}$alkyl,
$R_3$ is $C_{1-5}$alkyl, phenyl, or $C_{3-7}$cycloalkyl; or $C_{1-5}$alkyl or phenyl substituted with a group Y where Y is a group not reduced by the catalyst such as
(a) t-$C_4H_9(Me)_2SiO-$;
(b) halogen (F, Cl or Br);
(c) trifluoromethyl;
(d) $C_{1-3}$ alkoxy;
(e) $C_{1-3}$alkylcarbonyloxy
(f) phenylcarbonyloxy;
(g) $C_{1-3}$alkoxycarbonyl;
(h) phenyloxycarbonyl.

$R_4$ is H or $CH_3$ or $OSi(Me)_2t-C_4H_9$;
$R_5$ is H or $OSi(Me)_2t-C_4H_9$; provided that one and only one of $R_4$ and $R_5$ is $OSi(Me)_2t-C_4H_9$.

In one class of this embodiment, $R_2$ is H or $CH_3$, and $R_3$ is $CH_3CH_2$.

In a subclass are compounds (III) wherein:
a. $R_2$ is H, $R_4$ is $OSi(Me)_2t-C_4H_9$ and $R_5$ is H;
b. $R_2$ is $CH_3$, $R_4$ is $OSi(Me)_2t-C_4H_9$ and $R_5$ is H;
c. $R_2$ is $CH_3$, $R_4$ is $OSi(Me)_2t-C_4H_9$ and $R_5$ is $CH_3$;
d. $R_2$ is H, $R_4$ is H and $R_5$ is $OSi(Me)_2t-C_4H_9$;
e. $R_2$ is H, $R_4$ is $CH_3$ and $R_5$ is $OSi(Me)_2t-C_4H_9$;
f. $R_2$ is $CH_3$, $R_4$ is H and $R_5$ is $OSi(Me)_2t-C_4H_9$;
g. $R_2$ is $CH_3$, $R_4$ is $CH_3$ and $R_5$ is $OSi(Me)_2t-C_4H_9$.

Starting diene, lovastatin, wherein $R_1$ is methyl, $R_2$ is hydrogen, $R_3$ is ethyl, $R_4$ is methyl and $R_5$ is hydrogen is readily available or may be prepared according to the fermentation procedures disclosed in U.S. Pat. No. 4,231,938. Simvastatin, wherein $R_1$ is methyl, $R_2$ is methyl, $R_3$ is ethyl, $R_4$ is methyl and $R_5$ is hydrogen may be prepared from lovastatin following the procedure described in U.S. Pat. No. 4,582,915 or copending U.S. application Ser. No. 072066 filed July 10, 1987. Starting dienes wherein $R_4$ or $R_5$ is $CH_2OSi(Me)_2t-C_4H_9$ are prepared following the procedure outlined in copending U.S. Patent application Ser. No. 048136 filed May 15, 1987, followed by protection with t-$C_4H_9(Me)_2SiCl$. Dienes where both $R_4$ and $R_5$ are hydrogen may be prepared from the fermentation product compactin (also known as mevastatin) (Endo, et al, *J. Antibiot.*, 29, 1346 (1976)).

Compounds wherein $R_4$ or $R_5$ is $OSi(Me)_2t-C_4H_9$ can be prepared following the descriptions in U.S. Pat. Nos. 4,517,373 and 4,537,859 for preparing the C-6-hydroxyl derivatives followed by protection with t-$C_4H_9(Me)_2$SiCl.

Dienes with substituted acyl groups are synthesized using acyl chlorides, prepared by standard techniques, and the acylation procedure described by Hoffman et al., in U.S. Pat. No. 4,444,784 or that disclosed in copending U.S. patent application Ser. No. 038580 filed Apr. 15, 1987.

The catalyst is [Ir(COD)PCy$_3$(pyr)]PF$_6$ (COD=1,5-cyclooctadiene, PCy$_3$=tricyclohexylphosphine, pyr=pyridine) or [Rh(NBD)(DIPHOS-4)]BF$_4$. (NBD=norbornadiene, DIPHOS-4=1,4 bis(diphenylphosphino)-butane), preferably [Ir(COD)PCy$_3$(pyr)]PF$_6$. The iridium catalyst may be prepared following the procedure described by Crabtree et al., *J. Organomet. Chem.*, 135, 395 (1977). The rhodium catalyst can be prepared by the procedure outlined by Stille et al., *J. Org. Chem.*, 47, 468 (1982), and supplemented by Evans et al., *J. Am. Chem. Soc.*, 106, 3866 (1984).

The diene substrate and the iridium or rhodium catalyst in a mole percent of 0.1 to 10 mole percent catalyst to diene, preferably 2.5 mole percent catalyst to diene, is dissolved in dichloromethane, chloroform, chlorobenzene or a like solvent, preferably dichloromethane. The solution is reduced under atmospheric hydrogen pressure at a temperature of 25° to 80° C., preferably 25° C. After standard workup procedures, evaporation of solvent yields the desired 3,5 dihydro derivative.

The following Examples illustrate the present invention and as such are not to be considered as limiting the invention set forth in the claims appended hereto.

EXAMPLE 1

Preparation of 6(R) [2 [8(S) (2-methylbutyryloxy)-2(S),6(R)-dimethyl 1,2,3,5,6,7,8,8a(S)-octahydro-1(S)]ethyl]4(R) hydroxy -3,4,5,6 -tetrahydro -2H -pyran-2-one A solution of lovastatin (0.63 g, 1.56 mmole) in dichloromethane (15 ml) was purged with argon gas. 1,5-Cyclooctadiene(pyridine)(tricyclohexylphosphine)iridium(I) hexafluorophosphate (0.0313 g, 2.5 mole percent) was added and the solution reduced at ambient temperature under one atmosphere hydrogen pressure. H$_2$ uptake was very rapid in the first 50 minutes. After 1 hour and 37 minutes, the reaction was stopped and the solution evaporated in vacuo to a yellow oil which was taken up in diethyl ether (50 ml) and filtered through a one inch bed of Florisil ® (Magnesium silicate filter aid used herein to retain any catalyst complex which remained in solution). The filtrate was evaporated to give the title compound as a pale yellow oil. $^1$HNMR (300 MHz, CDCl$_3$) δ 5.48 (brs, 1H), 5.28 (m, 1H) 4.63 (m, 1H), 4.35 (m, 1H), 2.74 (dd, J=16,7Hz, 1H), 2.61 (dd, J=16, 4Hz, 1H), 1.22–2.45(m), 1.12 (d, J=7Hz, 3H), 1.0 (d, J=7Hz, 3H), 0.87 (t, J=7Hz, 3H), 0.82 (d, J=7Hz, 3H).

EXAMPLES 2–12

Following the procedure substantially as described in Example 1 but substituting for the mevinolin used as starting material therein, approximately equimolar amounts of structure (II) as described below there are prepared the corresponding 3,5-dihydro derivatives of structure (III).

|  | R$_1$ | R$_2$ | R$_3$ | R$_4$ | R$_5$ |
|---|---|---|---|---|---|
| Example 2 | CH$_3$ | CH$_3$ | CH$_3$CH$_2$ | CH$_3$ | H |
| Example 3 | CH$_3$ | H | CH$_3$CH$_2$ | CH$_2$OSi(Me)$_2$t-C$_4$H$_9$ | H |
| Example 4 | CH$_3$ | H | CH$_3$CH$_2$ | H | CH$_2$OSi(Me)$_2$t-C$_4$H$_9$ |
| Example 5 | CH$_3$ | CH$_3$ | CH$_3$CH$_2$ | CH$_2$OSi(Me)$_2$t-C$_4$H$_9$ | H |
| Example 6 | CH$_3$ | CH$_3$ | CH$_3$CH$_2$ | H | CH$_2$OSi(Me)$_2$t-C$_4$H$_9$ |
| Example 7 | CH$_3$ | H | CH$_3$CH$_2$ | CH$_2$OSi(Me)$_2$t-C$_4$H$_9$ | H |
| Example 8 | CH$_3$ | CH$_3$ | CH$_3$CH$_2$ | CH$_2$OSi(Me)$_2$t-C$_4$H$_9$ | H |
| Example 9 | CH$_3$ | H | CH$_3$CH$_2$ | H | CH$_2$OSi(Me)$_2$t-C$_4$H$_9$ |
| Example 10 | CH$_3$ | H | CH$_3$CH$_2$ | CH$_3$ | CH$_2$OSi(Me)$_2$t-C$_4$H$_9$ |
| Example 11 | CH$_3$ | CH$_3$ | CH$_3$CH$_2$ | H | CH$_2$OSi(Me)$_2$t-C$_4$H$_9$ |
| Example 12 | CH$_3$ | CH$_3$ | CH$_3$CH$_2$ | CH$_3$ | CH$_2$OSi(Me)$_2$t-C$_4$H$_9$ |

What is claimed is:
1. A process for the preparation of a compound of structural formula (III):

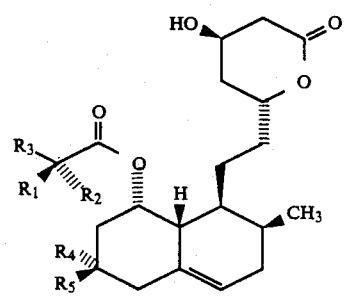

wherein:
R$_1$ is H or C$_{1-3}$alkyl;
R$_2$ is H or C$_{1-3}$alkyl;
R$_3$ is C$_{1-5}$alkyl, phenyl, or C$_{3-7}$cycloalkyl; or C$_{1-5}$alkyl or phenyl substituted with a group Y where Y is selected from the group consisting of:
(a) t-C$_4$H$_9$(Me)$_2$SiO—,
(b) halogen,
(c) trifluoromethyl,
(d) C$_{1-3}$alkoxy,
(e) C$_{1-3}$alkylcarbonyloxy,
(f) phenylcarbonyloxy,
(g) C$_{1-3}$alkoxycarbonyl,
(h) phenyloxycarbonyl;
R$_4$ is H or CH$_3$ or CH$_2$OSi(Me)$_2$t-C$_4$H$_9$ or OSi(Me)$_2$t-C$_4$H$_9$;
R$_5$ is H, or CH$_2$OSi(Me)$_2$t-C$_4$H$_9$ or OSi(Me)$_2$t-C$_4$H$_9$; provided that when either R$_4$ or R$_5$ is CH$_2$OSi(Me)$_2$t-C$_4$H$_9$ the other is H; and one and only one of R$_4$ and R$_5$ can be OSi(Me)$_2$t-C$_4$H$_9$.
which comprises:
contacting a compound of structural formula (II)

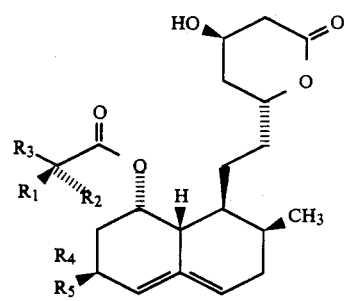

with 1,5-cyclooctadiene(pyridine)(tricyclohexylphosphine)iridium(I) hexafluorophosphate or norbornadiene-1,4-bis(diphenylphosphino)butanerhodium(I) tetrafluoroborate in a solvent, under an atmospheric pressure of hydrogen gas at 25° to 80° C.

2. A process of claim 1 wherein:
R$_4$ is H or CH$_3$ or CH$_2$OSi(Me)$_2$t-C$_4$H$_9$;
R$_5$ is H or CH$_2$OSi(Me)$_2$t-C$_4$H$_9$; provided that when either R$_4$ or R$_5$ is CH$_2$OSi(Me)$_2$t-C$_4$H$_9$ the other is H.

3. A process of claim 1 wherein the catalyst is 1,5-cyclooctadiene(pyridine)(tricyclohexylphosphine)iridium(I) hexafluorophosphate.

4. A process of claim 3 wherein the solvent is selected from dichloromethane, chloroform or chlorobenzene.

5. A process of claim 4 wherein the temperature is about 25° C., and the solvent is dichloromethane.

6. A process of claim 5 wherein the mole percent of catalyst to diene is about 2.5 mole percent.

7. A process of claim 1 wherein:
R$_1$ is CH$_3$,
R$_4$ is CH$_3$; and
R$_5$ is H.

8. A process of claim 7 wherein:
R$_3$ is C$_{1-5}$alkyl.

9. A process of claim 8 wherein the compound (III) prepared is selected from the group wherein:
a. R$_2$ is H and R$_3$ is CH$_3$CH$_2$;
b. R$_2$ is CH$_3$ and R$_3$ is CH$_3$CH$_2$.

10. A process of claim 1 wherein:
R$_1$ is CH$_3$,
R$_4$ is H or CH$_2$OSi(Me)$_2$t-C$_4$H$_9$;
R$_5$ is H or CH$_2$OSi(Me)$_2$t-C$_4$H$_9$; provided that at least one of R$_4$ or R$_5$ is H.

11. A process of claim 10 wherein:
R$_2$ is H or CH$_3$; and
R$_3$ is CH$_3$CH$_2$.

12. A process of claim 11 wherein the compound (III) prepared is selected from the group wherein:
a. R$_2$ is H,
R$_4$ is CH$_2$OSi(Me)$_2$t-C$_4$H$_9$ and $R_5$ is H;
b. $R_2$ is H,
$R_4$ is H and
$R_5$ is $CH_2OSi(Me)_2t\text{-}C_4H_9$;
c. $R_2$ is $CH_3$,
$R_4$ is $CH_2OSi(Me)_2t\text{-}C_4H_9$ and
$R_5$ is H;
d. $R_2$ is $CH_3$,
$R_4$ is H and
$R_5$ is $CH_2OSi(Me)_2t\text{-}C_4H_9$.

13. A process of claim 1 wherein:
$R_1$ is $CH_3$,
$R_4$ is H or $CH_3$ or $OSi(Me)_2t\text{-}C_4H_9$;
$R_5$ is H or $OSi(Me)_2t\text{-}C_4H_9$; provided that one and only one of $R_1$ and $R_2$ is $OSi(Me)_2t\text{-}C_4H_9$.

14. A process of claim 13 wherein:
$R_2$ is H or $CH_3$; and
$R_3$ is $CH_3CH_2$.

15. A process of claim 14 wherein the compound (III) prepared is selected form the group wherein:
a. $R_2$ is H, $R_4$ is $OSi(Me)_2t\text{-}C_4H_9$ and $R_5$ is H;
b. $R_2$ is $CH_3$, $R_4$ is $OSi(Me)_2t\text{-}C_4H_9$ and $R_5$ is H;
c. $R_2$ is H, $R_4$ is H and $R_5$ is $OSi(Me)_2t\text{-}C_4H_9$;
d. $R_2$ is H, $R_4$ is $CH_3$ and $R_5$ is $OSi(Me)_2t\text{-}C_4H_9$;
e. $R_2$ is $CH_3$, $R_4$ is H and $R_5$ is $OSi(Me)_2t\text{-}C_4H_9$;
f. $R_2$ is $CH_3$, $R_4$ is $CH_3$ and $R_5$ is $OSi(Me)_2t\text{-}C_4H_9$.

16. A process of claim 9 wherein the catalyst is 1,5 cyclooctadiene(pyridine)(tricyclohexylphosphine)iridium(I) hexafluorophosphate, the solvent is dichloromethane, the temperature is about 25° C. and the mole percent catalyst to diene is 2.5 mole percent.

17. A process of claim 12 wherein the catalyst is 1,5 cyclooctadiene(pyridine)(tricyclohexylphosphine)iridium(I) hexafluorophosphate, the solvent is dichloromethane, the temperature is about 25° C. and the mole percent catalyst to diene is 2.5 mole percent.

18. A process of claim 15 wherein the catalyst is 1,5-cyclooctadiene(pyridine)(tricyclohexylphosphine)iridium(I) hexafluorophosphate, the solvent is dichloromethane, the temperature is about 25° C. and the mole percent catalyst to diene is 2.5 mole percent.

* * * * *

UNITED STATES PATENT AND TRADEMARK OFFICE
CERTIFICATE OF CORRECTION

PATENT NO. : 4,826,999
DATED : May 2, 1989
INVENTOR(S) : A. E. DeCamp et al

It is certified that error appears in the above-identified patent and that said Letters Patent is hereby corrected as shown below:

At column 6, lines 5-14, please delete structure (II) and insert:

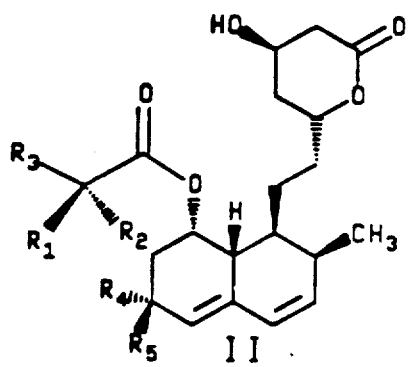

Signed and Sealed this

Thirteenth Day of March, 1990

Attest:

JEFFREY M. SAMUELS

Attesting Officer

Acting Commissioner of Patents and Trademarks